United States Patent
Campagna (10) Patent No.: US 7,598,737 B2
(45) Date of Patent: Oct. 6, 2009

(54) METHOD AND CONTROL DEVICE FOR DETERMINATION OF THE POSITION OF A LOCAL COIL IN A MAGNETIC RESONANCE APPARATUS

(75) Inventor: Swen Campagna, Engelthal (DE)

(73) Assignee: Siemens Aktiengesellschaft, Munich (DE)

( * ) Notice: Subject to any disclaimer, the term of this patent is extended or adjusted under 35 U.S.C. 154(b) by 176 days.

(21) Appl. No.: 11/592,463

(22) Filed: Nov. 2, 2006

(65) Prior Publication Data

US 2007/0103157 A1   May 10, 2007

(30) Foreign Application Priority Data

Nov. 2, 2005   (DE) .................. 10 2005 052 564

(51) Int. Cl.
G01V 3/00 (2006.01)
A61B 5/055 (2006.01)
(52) U.S. Cl. ................ 324/307; 324/318; 324/309; 600/410; 600/422
(58) Field of Classification Search ......... 324/318–322, 324/307–309; 600/410, 411, 422; 703/2; 382/128
See application file for complete search history.

(56) References Cited

U.S. PATENT DOCUMENTS

| | | | | |
|---|---|---|---|---|
| 5,936,406 | A * | 8/1999 | Potthast | 324/318 |
| 6,445,181 | B1 * | 9/2002 | Pelc et al. | 324/307 |
| 6,794,872 | B2 | 9/2004 | Meyer et al. | 324/318 |
| 6,822,447 | B1 * | 11/2004 | Yamagata | 324/318 |
| 6,946,836 | B2 * | 9/2005 | Kuhara | 324/307 |
| 7,023,208 | B2 * | 4/2006 | Kurimoto et al. | 324/314 |
| 7,026,818 | B2 * | 4/2006 | Machida et al. | 324/322 |
| 7,034,535 | B2 * | 4/2006 | Yamagata | 324/318 |
| 7,141,976 | B2 * | 11/2006 | Campagna | 324/318 |
| 7,145,338 | B2 * | 12/2006 | Campagna et al. | 324/318 |
| 7,183,770 | B2 * | 2/2007 | Graβlin et al. | 324/322 |
| 7,190,164 | B2 * | 3/2007 | Kuhara | 324/309 |
| 7,218,106 | B2 * | 5/2007 | Yasuhara et al. | 324/307 |
| 7,218,109 | B2 * | 5/2007 | Campagna | 324/309 |
| 7,336,076 | B2 * | 2/2008 | Kuhara | 324/318 |
| 2005/0083051 | A1 * | 4/2005 | Campagna et al. | 324/302 |
| 2005/0122108 | A1 * | 6/2005 | Yasuhara et al. | 324/318 |
| 2005/0253584 | A1 * | 11/2005 | Campagna | 324/318 |
| 2005/0264288 | A1 * | 12/2005 | Campagna et al. | 324/309 |
| 2005/0275402 | A1 * | 12/2005 | Campagna | 324/309 |
| 2006/0054810 | A1 * | 3/2006 | Grasslin et al. | 250/299 |
| 2007/0103157 | A1 * | 5/2007 | Campagna | 324/318 |
| 2007/0110290 | A1 * | 5/2007 | Chang et al. | 382/128 |
| 2007/0265813 | A1 * | 11/2007 | Unal et al. | 703/2 |
| 2008/0108891 | A1 * | 5/2008 | Campagna | 600/410 |

\* cited by examiner

Primary Examiner—Brij B. Shrivastav
Assistant Examiner—Tiffany A Fetzner
(74) Attorney, Agent, or Firm—Schiff Hardin LLP (57) ABSTRACT

In a method for determination of a position of a local coil on a bed in at least one spatial direction within a magnetic resonance scanner, a signal intensity value is initially, extracted from magnetic resonance measurements implemented with the appertaining local coil for acquisition of magnetic resonance images of an examination subject and/or for measurement of further system parameters at each of various positions of the recumbent bed relative to the tomograph. The functional dependency of the extracted signal intensity values on the position of the bed relative to the scanner is then determined. The position of the local coil on the bed is determined on the basis of the determined functional dependency. A corresponding control device for a magnetic resonance system and a computer program product implement the method.

17 Claims, 4 Drawing Sheets

METHOD AND CONTROL DEVICE FOR DETERMINATION OF THE POSITION OF A LOCAL COIL IN A MAGNETIC RESONANCE APPARATUS

BACKGROUND OF THE INVENTION

1. Field of the Invention

The invention concerns a method for determination of the position of a local coil on a patient bed in at least one spatial direction within a magnetic resonance tomograph apparatus. The invention moreover concerns a corresponding control device for a magnetic resonance system for determination of the position of a local coil in a scanner of a magnetic resonance system that implements such a method, a magnetic resonance system with such a control device as well as a corresponding computer program product that can be directly loaded into a processor of a programmable control device of a magnetic resonance system in order to implement such a method.

2. Description of the Prior Art

Modern magnetic resonance system normally operate with a number of various RF antennas (called coils in the following) for emission of radio-frequency pulses for exciting nuclei so as to emit magnetic resonance signals and/or for acquisition of the induced magnetic resonance signals. A magnetic resonance system normally has a larger whole-body coil (body coil) permanently installed in the magnetic resonance scanner. The whole-body coil is typically arranged cylindrically (for example with a structure known as a birdcage structure) around the patient acquisition chamber in which the patient is supported on a bed (often also called a patient positioning table) during the measurement. Furthermore, one or more small local coils or surface coils are frequently inserted into the magnetic resonance scanner. The local coils serve to acquire detailed images of body parts or organs of a patient that are located relatively near to the body surface. For this purpose the local coils are applied directly at the point of the patient at which the region to be examined is located. Given the use of such a local coil, in many cases RF energy is emitted with the whole-body coil (as a transmission coil) and the induced magnetic resonance signals are acquired with a local coil (as a reception coil).

For a magnetic resonance examination, it is important to know the exact position of the employed local coils relative to the bed (and thus relative to the patient). In principle, when the bed is mounted out of the scanner it is possible to manually measure the position of the coils using rulers, gauges, markings on the bed, etc. Such a measurement, however, is very complicated and additionally entails the risk that the measured positions are associated with the wrong coils, in particular given the usage of a number of coils, or given the usage of coil arrays composed of a number of coils. In principle, it is therefore simpler and safer to automatically determine the position of the local coils in the framework of a magnetic resonance measurement.

Such an automatic determination of the position of a local coil on a patient bed in a specific spatial direction can ensue, for example, according to a method described in DE 102 07 736 A1. A magnetic field gradient is applied in the appertaining spatial direction in which the position should be determined. A radio-frequency signal is then emitted with the whole-body coil or with a local coil, and an acquisition signal profile is measured along the magnetic field gradient by the appertaining local coil whose position is to be established. The position of the local coil in the appertaining spatial direction is determined with this signal profile.

A problem in the determination of the coil position according to this method occurs with regard to the essential determination of the support of the coil in the longitudinal direction of the bed (typically designated as the z-direction). The possibility exists that the coil is located entirely on the edge or outside of the scanner (and thus outside of the magnetic field) since the bed can be displaced (shifted) in the z-direction and is normally located only partially inside the scanner. If a local coil is located directly at the edge of the magnetic resonance scanner, the coil profile at the time varies unpredictably and chaotically. If the local coil is located outside of the scanner, a relevant coil profile can no longer be measured at all. This leads to the situation of a completely false position for such local coils being determined on occasion with conventional position determination methods.

These measurements therefore are normally supplemented by various quality criteria that are determined with the aid of additionally-acquired separate measurement values. Using these quality criteria, it can then be decided whether a measured signal profile represents a reasonable signal and thus can be used at all in a position determination algorithm in order to achieve a reliable result. This in turn reduces the number of the cases in which a result materializes at all. A number of measurements must additionally be implemented for determination of the coil position, which has an associated time loss.

SUMMARY OF THE INVENTION

An object of the present invention is to provide a fast and cost-effective method for automatic detection of the position of a local coil in which the local coil can be localized relatively safely and precisely, independent of its position on the bed, and wherein the aforementioned problems are avoided. Moreover, it is an object of the invention to specify a corresponding control device, a magnetic resonance system and a computer program product that enable the implementation of such a measurement.

In the inventive method, in a first step a signal intensity value is initially extracted from respective magnetic resonance measurements implemented with the appertaining local coil for acquisition of magnetic resonance images of an examination subject and for measurement of further system parameters at various positions of the bed relative to the scanner. The term "signal intensity value", means each scalar value that represents the signal intensity that is measured by the coil or is correlated with it. This means that no special measurement is implemented for the position determination. Instead, measurements to be implemented for other reasons are used and their measurement results are analyzed in an expert manner in order to acquire a signal intensity value for various positions of the local coil relative to the scanner. Advance measurements for acquisition of magnetic resonance images or the acquisition of further parameters are always implemented anyway for each magnetic resonance examination in order to establish specific parameters for the examination. The magnetic resonance images acquired in the framework of such measurements can be, for example, typical overview exposures (localizer scans) or the like. The further system parameters that are normally measured at the beginning of or before the implementation of the actual magnetic resonance examination can be measurements of the spatial dependency of resonance frequencies, of load ratios, or of field homogenization data, etc. that are determined in what are known as "adjustment measurements".

The functional dependency of the extracted signal intensity value on the position of the bed relative to the scanner is then determined in a further step.

Finally, the position of the local coil is determined on the basis of this determined functional dependency.

The advantages of this method are clear. The method is very fast since a dedicated measurement is no longer necessary for coil position determination and, instead of this, measurement data that are acquired for a different purpose anyway are interpreted in a suitable manner.

Due to the type of the method, a very reliable detection of whether a coil is located inside or outside of the scanner (meaning inside or outside of the magnetic field developed by the magnet in the scanner) is additionally possible.

A further advantage of the inventive method is that, due to the consideration of a number of measurement values at various positions (which is different than given the use of only one stationary exposure of a coil profile), the noise of individual measurements is automatically "cancelled" by the averaged use of the various measurements, and the position is determined with much greater precision than previously.

An inventive control device for a magnetic resonance system for (advantageously wholly automatic) determination of the position of a local coil on a recumbent bed within the magnetic resonance scanner of the magnetic resonance system has a signal evaluation unit that is fashioned such that it extracts a signal intensity value from the respective magnetic resonance measurements implemented with the appertaining local coils for acquisition of magnetic resonance images of an examination subject and/or for measurement of further parameters at various positions of the bed relative to the scanner. Moreover, the control device has a signal analysis unit that is fashioned such that the functional dependency of the extracted signal intensity values on the position of the bed relative to the scanner is determined. The control device also has a position calculation unit that determines the position of the local coil on the bed on the basis of the determined functional dependencies.

As explained above, the extracted signal intensity value can be an arbitrary scalar value that is a measure for a signal intensity measured at a specific position by the local coil.

In a preferred embodiment, the intensity maximum measured by the appertaining local coil is extracted as the signal intensity value from the magnetic resonance measurements. For this purpose, the signal evaluation unit has a maximum determination unit. This embodiment is particularly suited when total intensities are measured in the framework of the measurements used for the localization, such as, for example, in measurements with an FID sequence (FID=Free Induction Decay).

In alternative preferred exemplary embodiments, the respective intensities of a number of image points of a magnetic resonance image acquired with the appertaining local coil in the framework of the respective magnetic resonance measurement are integrated to determine the signal intensity value. An integration over all image points (meaning over the complete image that the respective local coil "sees") preferably ensues. For this purpose, for example, the brightness values of the image pixels (which brightness values are a measure of the intensities measured at the respective image points) are simply added. This method is particularly suitable when, for example, overview exposures are produced. The signal evaluation unit has in integration unit for this purpose.

The magnetic resonance measurements at the various positions of the bed relative to the scanner can ensue such that the bed approaches discrete positions at which a static measurement (or, if applicable, a number of measurements) is implemented. Measurements known as MDS measurements (MDS=Move During Scan) can likewise be used, for which the bed is moved continuously through the scanner during the measurement. Furthermore, virtually continuous measurements are also possible whereby the magnetic resonance measurements are implemented at a large number of closely adjacent points.

Typical magnetic resonance measurements for which sufficient measurements are implemented anyway at various positions of the bed before or at the beginning of an examination are magnetic resonance measurements for generation of overview exposures, for example what are known as "whole body localizers". Further measurement methods suitable for this are adjustment measurements such as, for example, an MDS adjustment measurement in which the resonance frequencies and the load ratios are measured in a spatially-dependent manner and a rough image has already also been acquired in order to then utilize these data for a later MDS measurement. Measurements can thereby be used in which the entire volume is excited in the tomograph, such as, for example, in the already-cited FID measurements, also measurements in which only a part of the volume is excited, for example a cube a few cubic centimeters in size or a transversal slice within the entire examination volume in the tomograph (such as, for example, given a STEAM measurement (STEAM=Simulated Echo Acquisition Mode).

In the implementation of the inventive method, it is possible to use extracted intensity values from different measurements. The measurements in principle can even be implanted with different measurement methods, i.e. (for example) various pulse sequences). The ratios of the intensity values that can be achieved with the various measurement methods relative to one another must then be known in order to be able to compare or to normalize to one another the intensity values from the various measurements. For the inventive position determination, magnetic resonance measurements are therefore preferably used that have been respectively implemented with the same measurement method at the various positions of the bed relative to the scanner.

Since, as described, it is possible to extract intensity values for the inventive method from the most varied measurements, and various methods for extraction of the intensity values can be advantageous depending on the type of the measurement, the control device has a decision unit in order to establish in which manner the intensity values are extracted from a measurement. Such a decision unit can be activated, for example by an operator such that the operator can ultimately provide the manner by which the extraction of the intensity values ensues for a specific measurement. Preferably, however, this decision unit decides in a wholly automatic manner, for example on the basis of the knowledge about the implemented measurements. For example, the manner by which the intensity values are to be extracted for each type of measurement, and whether the data are, for example, supplied to the maximum determination unit in order to extract the intensity maximum as the signal intensity value or, for example, to an integration unit in order to integrate the intensities of a number of image points from the acquired magnetic resonance images can be stored in a table to which the decision unit has access.

The evaluation of the functional dependency of the extract signal intensity values on the position of the bed relative to the scanner can ensue in various manners.

For example, the position value of the bed relative to the scanner can be precisely used for determination of the position of the local coil on the bed at which the extracted signal intensity values exhibit a maximum, dependent on the position of the bed. This means that the curve of the signal intensity values is checked for its maximum value dependent on the value of the position of the bed, and the local coil position on the bed is determined in this manner.

Alternatively or additionally, a rising and/or falling edge of the curve of the extracted signal intensity values can be analyzed dependent on the bed position in the scanner to determine the position of the local coil on the bed. For example, in a preferred embodiment the point of half of the curve maximum is determined. The coil position on the bed can already be derived on the basis of such an edge position.

In a preferred method for determination of the position of the local coil in the bed, a width of the curve of the signal intensity values is considered dependent on the bed position. This is possible, for example, without further measures when the positions of the edges are known since then the width simply corresponds as the interval between the edges. The FWHM (Full Width at Half Maximum) is preferably used as the curve width), meaning that the distance is determined between the points of half of the curve maximum.

In particular, the middle point of the curve of the extracted signal intensity values, depending on the bed position, can also be used to determine the local coil on the bed. This can ensue, for example, on the basis of analysis of the edges.

For a particularly exact consideration, the results of these analyses depend on, among other things, the spatial adjustment of the magnets in the scanner. This adjustment can be different for various scanners of the same design. An offset value is therefore advantageously taken into account in the determination of the position of the local coil on the bed on the basis of the functional dependency of the extracted signal intensity values on the bed position. This offset value is system-dependent and takes into account the spatial adjustment of the magnets in the scanner.

The components required for implementation of the invention in a magnetic resonance system, such as the signal evaluation unit with the maximum value determination unit, the integration unit and the decision unit as well as the signal analysis unit and the position calculation unit, can be realized completely or in a predominant part in the form of software components. Typical magnetic resonance systems have programmable control devices anyway, such that the invention is preferably realized in this manner by suitable control software. This means that a corresponding computer program product (computer-readable medium encoded with a data structure) is directly loaded into the processor of a programmable control device of the appertaining magnetic resonance system, the computer program product comprising program code in order to implement the inventive method. Existing control devices or magnetic resonance systems thus can easily be retrofitted (upgraded) for implementation of the inventive method.

DESCRIPTION OF THE PREFERRED
EMBODIMENTS

Figure 1:
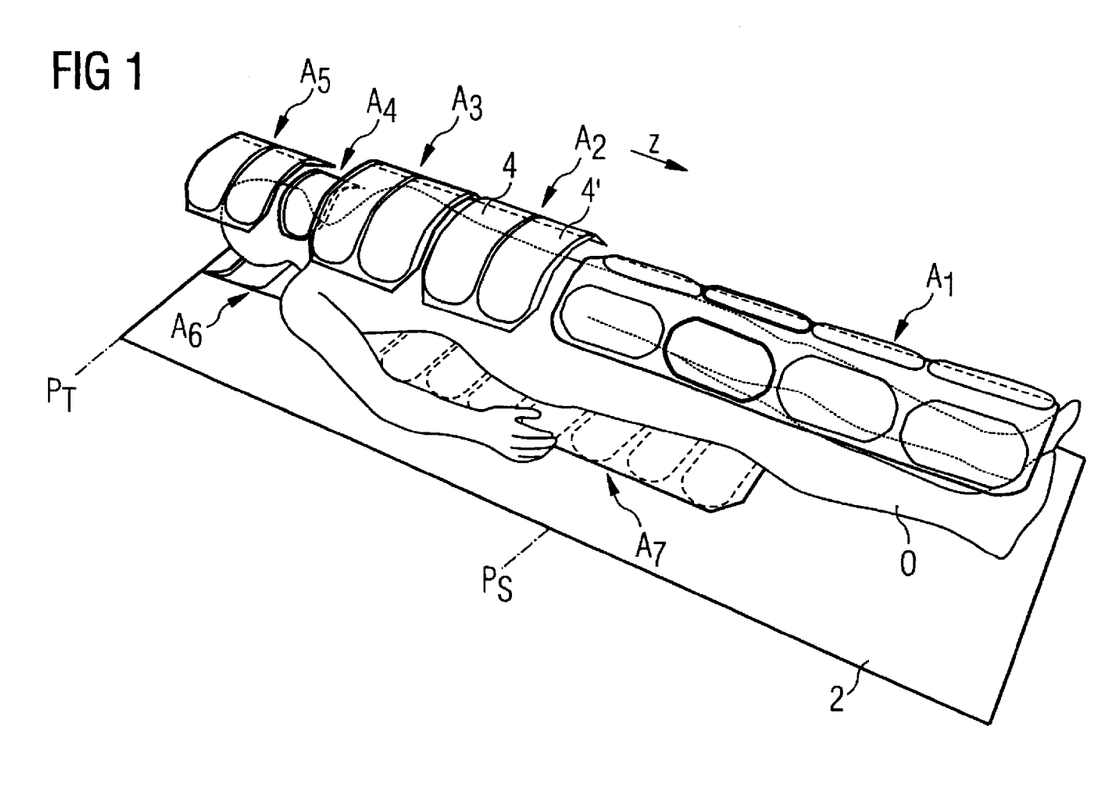
FIG. 1 is a perspective schematic representation of a patient on a bed with a number of local coil arrays.

FIG. 1 schematically shows a typical examination situation in which a patient O (or, respectively, a test subject) lies on a bed 2 and a number of local coil arrays $A_1, A_2, A_3, A_4, A_5, A_6, A_7$ are positioned both under the patient O and on the patient O. Such a local coil array $A_1, A_2, A_3, A_4, A_5, A_6, A_7$ normally has a number of individual local coils. In the shown case, a large array $A_7$ with eight individual coils lies below the patient O in the spinal column region up to the knee region. Two arrays $A_5, A_6$ with two coils respectively lie below the head and on the face of the patient O, with which two arrays $A_5, A_6$ images of the head of the patient O are acquired. A further array $A_4$ (here only one coil) is placed on the neck of the patient O. Two arrays $A_2, A_3$ with respectively two larger local coils are furthermore located on the chest area and abdomen area of the patient O. A local coil array $A_1$ with eight local coils in total is placed on the legs of the patient O.

For an examination, the positions of both local coils 4, 4' (located on the abdomen of the patient O) within the local coil array $A_2$ must now be determined, for example. This initially involves determining only the position $P_S$ in the z-direction relative to the position $P_T$ of the head end (head) of the bed 2, i.e. relative to the origin of the recumbent bed coordinate system. It is clear that the selection of this origin at the head end of the bed 2 is arbitrary and that, in principle, the position can also be determined in any other arbitrary bed coordinate system, for example with an origin at the foot end or in the middle of the recumbent bed 2.

Figure 2:
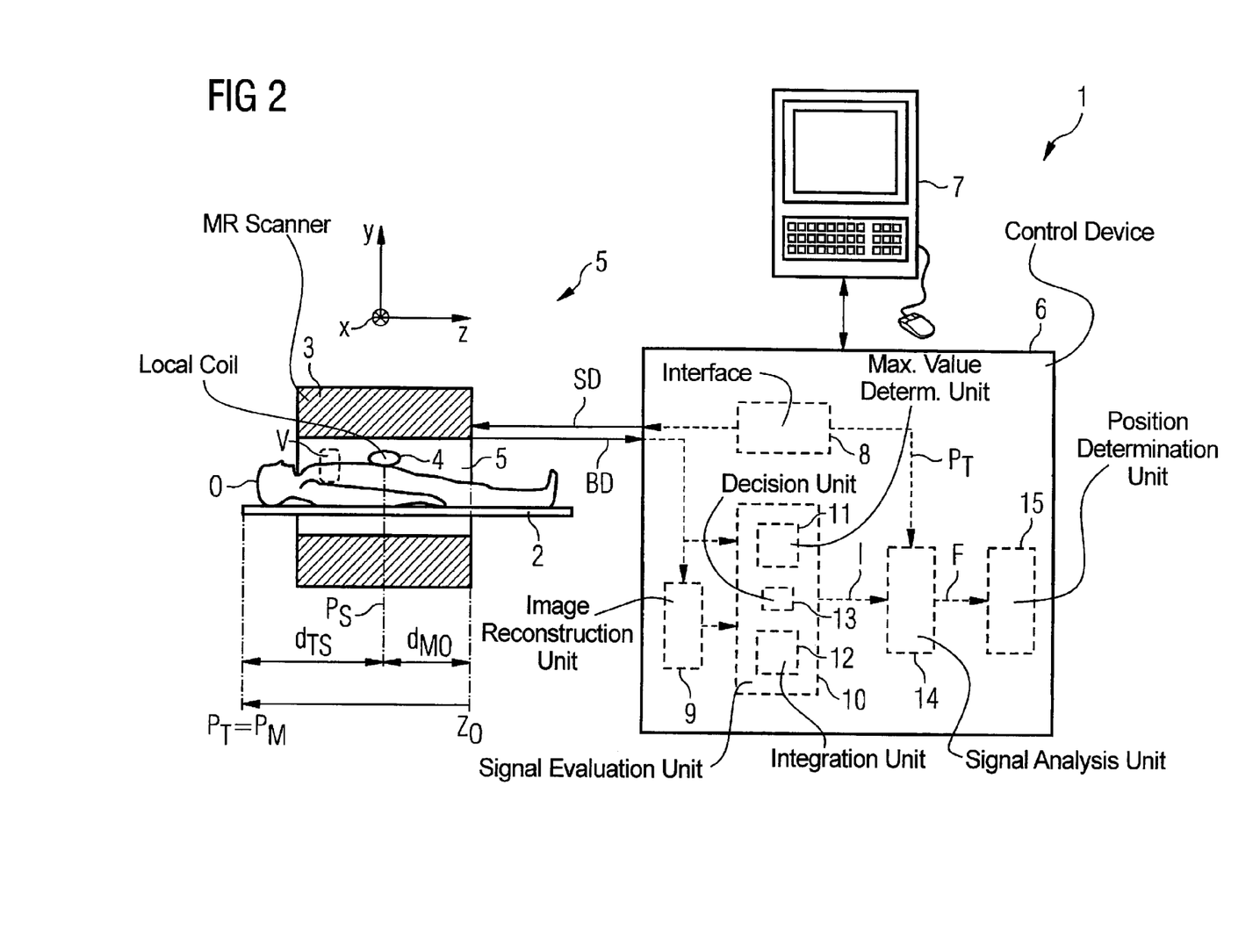
FIG. 2 is a schematic representation of an inventive magnetic resonance examination system.

FIG. 2 shows an exemplary embodiment for a magnetic resonance system 1 in which an automatic determination of the position of the local coil 4 according to the inventive method is possible. For better clarity, only one local coil 4 is plotted in this FIG. 2. The basic component of this magnetic resonance system 1 is the magnetic resonance scanner 3 in which the patient O on bed 2 is positioned in an annular basic field magnet (not shown in detail) that surrounds the measurement space 5.

The bed 2 can be displaced in the longitudinal direction, i.e. along the longitudinal axis of the scanner 3. This direction is designated as the z-direction in the spatial coordinate system (likewise shown). A whole-body coil 16 with which radio-frequency pulses can be emitted and received is located within the basic field magnet in the scanner. The scanner 3 also has gradient coils in a typical manner (not shown in FIG. 2) in order to be able to apply a magnetic field gradient in each of the spatial directions x, y, z.

The scanner 3 is activated by a control device 6 that here is shown separate therefrom. A terminal 7 is connected to the control device 6. This terminal 7 has a screen, a keyboard and a display apparatus for a graphical user interface, for example a mouse or the like. The terminal 7 serves as, among other things, a user interface via which an operator operates the control device 6 and therewith the scanner 3. Both the control device 6 and the terminal 7 can also be integral components of the scanner 3.

The magnetic resonance system 1 also has all further typical components or features such as, for example, interfaces for connection of a communication network, for example of an image information system or the like. These components are not shown in FIG. 2 for better clarity.

An operator can communicate with the control device 6 via the terminal 7 and thus arrange for the implementation of the desired measurements by entering control data SD into the control device 6 via a suitable interface 8 such that the required radio-frequency pulse sequences are emitted by the antenna and the gradient coils are switched in a suitable manner. The raw image data BD from the scanner 3 are also acquired by the control device 6. The images can then be reconstructed in an image data reconstruction unit 9. These images are shown, for example, on the screen of the terminal 7 and/or stored in a memory or sent over a network.

In the shown exemplary embodiment the control device 6 is designed such that able to determine (in a wholly automatic manner) the position $P_S$ of a local coil 4 which is located on the patient O relative to the bed 2. The position $P_S$ is thereby determined in the z-direction with the inventive method. The determined position specification can relate to the position $P_T$ of a fixed point on the bed 2, here (as described above) to the head-side front end of the bed 2. This fixed point relative to the recumbent bed 2 thus forms an origin for the bed coordinate system that moves with the bed 2. The position $P_S$ of the local coil 4 in this bed coordinate system can then be determined as a distance $d_{TS}$ relative to this fixed point.

As mentioned above, the bed 2 can be moved in a motorized manner in the z-direction within the scanner 3. With the aid of the interface 8 of the control device, the bed 2 can be automatically moved into and out of the scanner 3 or it can occupy arbitrary positions within the scanner 3 depending on whether this is necessary for the measurements to be implemented. The bed coordinate system (and thus its origin $P_T$) thereby moves relative to the scanner 3. The position of the bed 2 relative to the scanner therefore can be determined relative to an origin $z_o$ of a fixed "scanner coordinate system". Here an edge of the scanner 3 is selected as an origin $z_o$ of the scanner coordinate system. In principle, this is purely arbitrary, meaning that an arbitrarily different point can also be selected.

For determination of the position $P_s$ of the local coil 4 on the bed 2 the raw image data BD or (alternatively or additionally) the generated image data are passed to the image reconstruction unit 9.

This signal evaluation unit 10 (which, for example, can be fashioned in the form of a software module that is implemented on a suitable processor of the control device 6) here includes a maximum value determination unit 11, for example in the form of a software sub-module. In this maximum value determination unit 11, an intensity maximum respectively measured by the appertaining local coil can be extracted as a signal intensity value from the image data or the raw image data.

The signal evaluation unit 10 (for example in the form of a further software sub-module) can include an integration unit 12 that integrates the brightness values of the individual image pixels in a magnetic resonance image acquired with the appertaining local coil and thus determines a signal intensity value.

In order to decide whether the signal intensity value is reached by an integration of individual image points or an intensity maximum is used as a signal intensity value, the signal evaluation unit 10 has a decision unit 13. The evaluation method that is used and the manner of measurement are stored in this decision unit 13.

An extraction of the signal intensity value ensues for each of the measurements implemented at various positions of the bed 2 relative to the scanner 3, or given an MDS measurement, the incoming measurement data of the appertaining coil are correspondingly analyzed in an ongoing manner in order to extract the intensity values.

The intensity values I are then passed to a signal analysis unit 14. This signal analysis unit 14 can likewise be realized in the form of a software component. From the interface 8 this signal analysis unit 14 can obtain the positions $P_T$ of the recumbent bed 2 relative to the scanner 3, the positions $P_T$ being applicable for the individual measurements or intensity values. This is unproblematical since the position $P_T$ of the bed 2 relative to the scanner 3 is controlled by the interface 8.

The association of the intensity values I with the bed position $P_T$ then ensues in the signal analysis unit 14 in order to determine the functional dependency of the intensity values I on the bed position $P_T$, meaning that a corresponding function F is determined. This function F is then passes to a position determination unit 15 for further analysis.

The further procedure in the position determination unit 15 given the analysis of the function F for determination of the local coil position $P_S$ on the bed 2 is explained in detail in the following using actual test measurements with reference to FIGS. 3 through 5:

The signal was measured with a test design in which a body matrix coil with two coil elements (which here form the local coils whose positions are to be measured) was placed on a ball (spherical) phantom. This design essentially corresponds to the situation shown in FIG. 1; however, the local coil array $A_2$ is not placed on the abdomen of a patient O but rather on a phantom. Measurements at various positions $P_T$ of the recumbent bed 2 relative to the scanner 3 were respectively implemented with both coil elements in two measurement passes with different methods.

Figure 3:
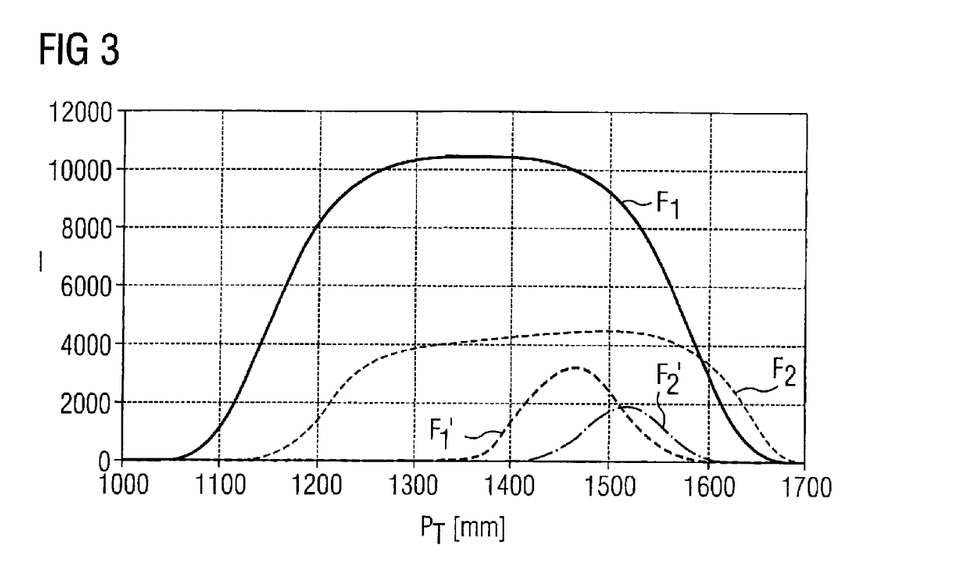
FIG. 3 shows the functional dependency of the signal intensity values of two different local coils dependent on the bed position, the signal intensity values respectively being extracted from an FID measurement (functions $F_1$ and $F_2$), and from a STEAM measurement (functions $F_1'$ and $F_2'$), with the local coils respectively moved completely through the scanner once.
Figure 4:
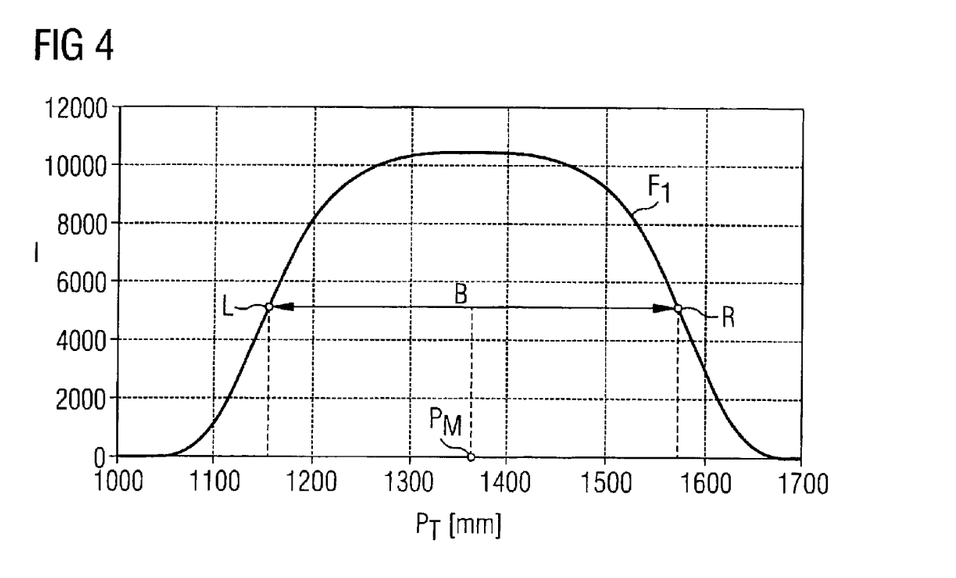
FIG. 4 shows the function $F_1$ from FIG. 3 for explanation of the evaluation thereof for the local coil position determination.

FIG. 3 shows two corresponding functions $F_1$, $F_2$, $F_1'$, $F_2'$ for each of the two coil elements, which functions $F_1$, $F_2$, $F_1'$, $F_2'$ respectively reflect the dependency of the intensity values I (extracted from the measurements implemented with the various measurement methods) on the recumbent bed position $P_T$. The functions $F_1$ and $F_1'$ respectively show the intensity values I (in relative, arbitrary units) of the first coil element and the functions $F_2$ and $F_2'$ of the intensity values I (in relative, arbitrary units) of the second coil element dependent on the position $P_T$ of the head end of the bed relative to the origin $z_o$ of the scanner coordinate system (see FIG. 2). The scale first begins at 1000 mm for better representation capability.

The measurements from which both broader functions $F_1$, $F_2$ were extracted are simple FID measurements that are not spatially selective, i.e. in which the entire measurement volume is uniformly excited. The local coils therefore see precisely one significant signal as soon as they are inside the scanner 3, i.e. inside the magnet. The curve of the functions $F_1$, $F_2$ reflects this very well.

In order to obtain both other functions $F_1'$, $F_2'$ shown in FIG. 3 that were generated (as stated) in the same test design for these same local coils, the intensity values were extracted from what is known as a STEAM frequency adjustment measurement. Given such a measurement the entire measurement volume 5 is not excited within the scanner 3; rather, only a specific smaller excitation region (as this is schematically shown in FIG. 2 by the excitation region V with a dashed border) is spatially-selectively excited. The intensity signal of the respective coil therefore increases precisely when the local reception coil enters into the selected excitation region V and correspondingly decreases when the local reception coil exits again from the excitation region. The function is consequently offset from the middle point of the magnet at the excited region. The width of the functions $F_1'$, $F_2'$ corresponding to the excited slice thickness is additionally narrower than the width of the functions $F_1$, $F_2$ that was extracted from measurements with an excitation of the complete measurement volume of the magnet. The total intensity is moreover not as high.

However, all functions $F_1$, $F_2$, $F_1'$, $F_2'$ contain all essential information for determination of the local coil position $P_S$ relative to the bed 2. Aside from the FID measurements and STEAM measurements cited above, however, any other measurements can also be used as a basis for generation of suitable functions.

Various procedures are conceivable in order to determine the positions $P_S$ of the local coils relative to the recumbent bed 2 from the functions $F_1$, $F_2$, $F_1'$, $F_2'$. One possibility is shown in FIG. 4 in the example of the function $F_1$ (generated from the FID measurement) of the first local coil.

For this a left point L and a right point R at which the function $F_1$ reaches half of its maximum are determined on the edges of the function $F_1$ by means of what is known as an FWHM method. The width B (FWHM=Full Width at Half Maximum) of the function $F_1$ between the two edges can be determined with these FWHM points L, R. The middle point between the two FWHM points L and R, meaning the point on the half width B, reflects the position $P_M$ at which the local coil is located exactly in the middle of the magnet. This point essentially corresponds to the middle of the scanner 3. In order to taken into account the individual adjustment of the magnet in the scanner 3, the determined point $P_M$ can be corrected as needed by a system-specific offset value. In order to be able to better take into account asymmetries, it is also possible to implement such a system-specific correction at the positions of both FWHM points L, R on both edges of the function $F_1$ instead of implementing a later correction of the middle point P.

The situation in which the local coil 4 (whose position is to be determined) is located in the middle of the scanner 3 is shown in FIG. 1. Here the position $P_T$ of the recumbent bed 2 relative to the apparatus origin $z_0$ corresponds exactly to the value $P_M$. Only the distance $d_{M0}$ of the middle point of the scanner 3 relative to the selected coordinate origin $z_0$ of the tomograph coordinate system must then still be taken into account. In the present case the distance $d_{M0}$ must be abstracted from the determined value $P_M$. As a result one then directly obtains the relative position $P_S$ of the local coil 4 relative to the bed coordinate system (i.e. here relative to the head end of the bed 2). Such a translation (conversion) is naturally not needed when the middle point of the scanner 3 is selected as the coordinate origin of the scanner coordinate system. The evaluation of the function $F_2$ for the second local coil can ensue in the same manner. Given a comparison of both functions $F_1$, $F_2$, it can also immediately be recognized very well from FIG. 3 that both local coils are offset by approximately 7.5 cm relative to one another.

The evaluation of the function $F_1'$, $F_2'$ from the STEAM measurements can also ensue in the same manner, as this was described using the function $F_1$. Due to the displacement of the excitation profile, only an offset is to be taken into account. However, this is not a problem since the control device itself determines in which spatial region the excitation ensues given the respective measurement, such that these values can be assumed.

Figure 5:
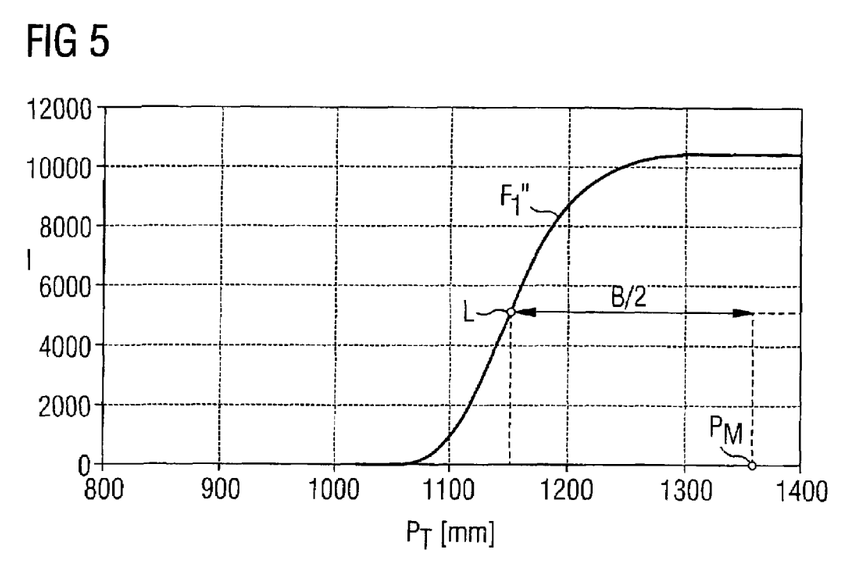
FIG. 5 shows the functional dependency of the signal intensity values of a localization dependent on the bed position as in FIG. 3, but the local coil was moved only into the scanner in the magnetic resonance measurements, but not completely therethrough.

FIG. 5 shows a similar measurement with the same test design as used for determination of the function $F_1$, but the local coil is moved into scanner 3 only once but not completely moved through it. The coil position can also already be determined relatively well from such a measurement, even if a complete measurement with a complete pass of the coil through the scanner 3 is naturally more precise. For example, for evaluation of such a half-side function $F_1''$ a FWHM point (here the left point L) is determined again on the edge of the function $F_1''$. This is possible since, at the function $F_1''$, it can be recognized relatively well when it has reached the upper plateau. The width B of the function is either a system property (for example when the entire measurement volume is excited) or a property dependent on the measurement method, namely on the width of the excitation volume. These parameters are normally known. It is therefore possible to find the sought middle point of the function $P_M$ solely from one of the FWHM points L, R using the half width B and thus to derive the coil position $P_s$ relative to the bed 2 as described above.

A precise coil position determination is possible with the inventive method in a simple and very quick manner since no additional measurements must be implemented. The method is additionally very reliable since no thresholds, weighting factors etc. whatsoever are required. Given a utilization of measurement signals from only one measurement type, the method is intrinsically self-weighting since the signals of one coil are only considered relative to itself and only such an individual data set must be considered in a self-contained manner. Due to the nature of the method an assured detection as to whether a coil is located inside or outside of the magnet is in particular possible. In many cases, solely this information is already sufficient for further steps since such information is for the most part acquired with difficulty and with little reliability given a singular stationary acquisition to be implemented according to the previous method. In the event that a very precise position of the coil (possibly including a detailed two- or three-dimensional exposure profile) is necessary for particular cases. A combination of the reliable position determination described here with such a method is also conceivable. In a first step, the position is then reliably determined with the aid of the inventive method without measurement time having to be applied for this. In a second step, a targeted refinement or expansion of the results is then implemented as needed and, in most cases, via additional expenditure of measurement time. By the evaluation in the first stop it can easily be assured that the coil is located within the excited region in order to preclude errors.

The method workflow described in detail in the preceding as well as the shown magnetic resonance system are only exemplary embodiments which can be modified by the those skilled in the art without departing from the scope of the invention. Numerous other procedures for determination of the coil position from the various functions are in particular also possible. However, the central point is the use of the described function as an actual information source, this function already being extracted from data determined anyway without additional measurements.

Although the invention was predominantly described in an example of magnetic resonance systems in the medical field, the possibilities for use of the invention are not limited to this field; rather, the invention can likewise also be used in scientific and/or industrial systems.

I claim as my invention:

1. A method for determining a position of a local coil on a bed within a magnetic resonance scanner that is movable relative to the magnetic resonance scanner, said magnetic resonance scanner also comprising a processor, said method comprising the steps of:

placing a local coil at a position on the patient bed, said position initially being unknown to the processor of the magnetic resonance scanner;

moving said bed together with said local thereon through a plurality of positions relative to said scanner;

at each of said plurality of positions, exciting nuclear spins in an examination subject on the bed using a transmitting antenna other than said local coil to cause magnetic resonant signals to be generated in the subject, and also at each of said plurality of positions, detecting said magnetic resonance signals with said local coil to obtain respective magnetic resonance measurement signals;

in said processor, extracting a signal intensity value for said local coil from said magnetic resonance measurement signals and determining a dependency of the extracted signal intensity values on the respective positions of the bed relative to the scanner; and in said processor, from the determined dependency, identifying a position, in at least one spatial direction, of the local coil on the bed and generating a signal, in a form selected from the group consisting of a stored signal and a signal emitted from the processor, representing said position in a form suitable for use in image acquisition or image reconstruction.

2. A method as claimed in claim 1 comprising extracting an intensity maximum from said magnetic resonance measurement as said signal intensity value.

3. A method as claimed in claim 1 comprising obtaining an integral over a number of image points of a magnetic resonance image acquired with said local coil in said magnetic resonance measurement, as said signal intensity value.

4. A method as claimed in claim 1 comprising executing each magnetic resonance measurement at the respective positions of the bed using the same magnetic resonance measurement technique.

5. A method as claimed in claim 1 comprising executing the respective magnetic measurements at said positions of said bed to obtain an overview exposure of a subject on the bed.

6. A method as claimed in claim 1 comprising executing the respective magnetic measurement resonance at the positions of the bed to obtain adjustment measurement for a subsequent acquisition of diagnostic magnetic resonance data.

7. A method as claimed in claim 1 comprising, in said processor, determining said position of said local coil from the determined dependency by identifying a position of the bed relative to the scanner at which the extracted signal intensity value exhibits a maximum.

8. A method as claimed in claim 1 comprising, in said processor, analyzing a rising edge or a falling edge of a curve representing the determined dependency to determine said position of said local coil.

9. A method as claimed in claim 1 comprising, in said processor, analyzing a width between a point on a rising edge of a curve representing the determined dependency, and a point on a falling edge of said curve, to determined said position of said local coil.

10. A method as claimed in claim 9 comprising, in said processor, using a middle point on said rising edge and a middle point on said falling edge to determine said width.

11. A method as claimed in claim 1 wherein said scanner produces an offset value, unique to said scanner, on the respective magnetic resonance measurements, and comprising, in said processor, taking said offset into account in determining said position of said local coil on said bed from the determined dependency.

12. A control device configured for determining a position of a local coil on a bed within a magnetic resonance scanner that is movable relative to the magnetic resonance scanner, said local coil being placed at a position on the patient bed, said position initially being unknown to the processor of the magnetic resonance scanner, said control device being configured to:

move said bed together with said local thereon through a plurality of positions relative to said scanner;

at each of said plurality of positions, operate said magnetic resonance scanner to excite nuclear spins in an examination subject on the bed using a transmitting antenna other than said local coil to cause magnetic resonant signals to be generated in the subject, and also at each of said plurality of positions, detect said magnetic resonance signals with said local coil to obtain respective magnetic resonance measurement signals;

extract a signal intensity value for said local coil from said magnetic resonance measurement signals and determine a dependency of the extracted signal intensity values on the respective positions of the bed relative to the scanner; and from the determined dependency, identify a position, in at least one spatial direction, of the local coil on the bed and generate a signal, in a form selected from the group consisting of a stored signal and a signal emitted from the control device, representing said position in a form suitable for use in image acquisition or image reconstruction.

13. A control device as claimed in claim 12 wherein said control device is further configured to extract an intensity maximum from said magnetic resonance measurement as said signal intensity value.

14. A control device as claimed in claim 12 wherein said control device is further configured to obtain an integral over a number of image points of a magnetic resonance image acquired with said local coil in said magnetic resonance measurement, as said signal intensity value.

15. A control device as claimed in claim 12 wherein said control device comprises a decision unit that identifies a type of said magnetic resonance measurement from which the signal intensity value is extracted.

16. A magnetic resonance system comprising:

a magnetic resonance scanner;

a patient bed that is movable relative to the magnetic resonance scanner;

a processor; a local coil on said patient bed that is moveable with said patient bed in said scanner;

a transmitting antenna other than said local coil;

said local coil being at a position on the patient bed, said position initially being unknown to the processor of the magnetic resonance scanner; said processor being configured to move said bed together with said local coil thereon through a plurality of positions relative to said scanner;

said processor being configured to operate said magnetic resonance scanner to excite at each of said plurality of positions, nuclear spins in an examination subject on the bed using the transmitting antenna other than said local coil to cause magnetic resonant signals to be generated in the subject, and also at each of said plurality of positions, to detect said magnetic resonance signals with said local coil to obtain respective magnetic resonance measurement signals;

said processor being configured to extract a signal intensity value for said local coil from said magnetic resonance measurement signals and configured to determine a dependency of the extracted signal intensity values on the respective positions of the bed relative to the scanner; and said processor being configured to identify, from the determined dependency, a position, in at least one spatial direction, of the local coil on the bed and to generate a signal, in a form selected from the group consisting of a stored signal and a signal emitted from the processor, representing said position in a form suitable for use in image acquisition or image reconstruction.

17. A computer-readable medium that determines a position of a local coil on a bed within a magnetic resonance scanner that is movable relative to the magnetic resonance scanner, said magnetic resonance scanner also comprising a processor, said local coil being at a position on the patient bed, said position initially being unknown to the processor of the magnetic resonance scanner, said computer-readable medium being encoded with programming instructions that cause said processor to:

move said bed together with said local thereon through a plurality of positions relative to said scanner;

at each of said plurality of positions, operate said magnetic resonance scanner to excite nuclear spins in an examination subject on the bed using a transmitting antenna other than said local coil to cause magnetic resonant signals to be generated in the subject, and also at each of said plurality of positions, to detect said magnetic resonance signals with said local coil to obtain respective magnetic resonance measurement signals;

in said processor, extract a signal intensity value for said local coil from said magnetic resonance measurement signals and determine a dependency of the extracted signal intensity values on the respective positions of the bed relative to the scanner; and in said processor, from the determined dependency, identify a position, in at least one spatial direction, of the local coil on the bed and generate a signal, in a form selected from the group consisting of a stored signal and a signal emitted from the processor, representing said position in a form suitable for use in image acquisition or image reconstruction.

* * * * *